United States Patent [19]
Imperante et al.

[11] Patent Number: 5,859,161
[45] Date of Patent: Jan. 12, 1999

[54] SILICONE PHOSPHATE ESTERS AS IRRITATION MITIGANTS

[75] Inventors: John Imperante, Lebanon, N.J.; Anthony J. O'Lenick, Jr., Lilburn, Ga.

[73] Assignees: Phoenix Chemical, Somerville, N.J.; Lambent Technologics Inc, Norcross, Ga.

[21] Appl. No.: 161,418

[22] Filed: Dec. 6, 1993

[51] Int. Cl.$^6$ .................................................. C08G 77/04
[52] U.S. Cl. ........................ 528/25; 514/887; 514/772.3; 424/78.05; 528/30; 528/23
[58] Field of Search .................. 424/78.05; 514/887, 514/772.3; 528/25, 30, 23

[56] References Cited

U.S. PATENT DOCUMENTS

| | | | |
|---|---|---|---|
| 3,961,044 | 6/1976 | Kelly et al. | 424/78 |
| 4,960,845 | 10/1990 | O'Lenick, Jr. | 528/25 |
| 5,070,171 | 12/1991 | O'Lenick, Jr. | 528/33 |
| 5,091,493 | 2/1992 | O'Lenick, Jr. et al. | 528/30 |
| 5,149,762 | 9/1992 | O'Lenick, Jr. | 528/25 |

*Primary Examiner*—Melvyn I. Marquis

[57] ABSTRACT

The present invention relates to a series of novel silicone phosphate esters which mitigate eye and skin irritation when used in synergistic combinations with fatty alcohol sulfates and fatty alcohol ether sulfates. These materials form complexes which have surprisingly low irritation properties.

9 Claims, No Drawings

SILICONE PHOSPHATE ESTERS AS IRRITATION MITIGANTS

BACKGROUND OF THE INVENTION

(1) Field of Invention

The present invention relates to a series of novel silicone phosphate esters which mitigate eye and skin irritation when used in synergistic combinations with fatty alcohol sulfates and fatty alcohol ether sulfates. The compounds useful in to form synergistic combinations with fatty alcohol sulfates and fatty alcohol ether sulfates are the topic of U.S. Pat. No. 5,070,171 issued to O'Lenick, Jr. and U.S. Pat. No. 5,149,762 likewise issued to O'Lenick, Jr. which are incorporated herein by reference. These compounds are referred to in this specification as silicone phosphate esters. They are items of commerce and are manufactured by Siltech Inc. of Norcross Ga., to whom the above patents are assigned.

The compounds useful in preparing the synergistic blends of the present invention are fatty alcohol sulfates or fatty alcohol ether sulfates and silicone phosphate esters. The silicone phosphate esters are items of commerce and are prepared by the phosphation of a pendant hydroxyl group which is present on a silicone polymer.

We have surprisingly learned that if the silicone phosphate esters described in the above mentioned patents are mixed with fatty alcohol sulfates or fatty alcohol ether sulfates prior to contact with the eye and skin that the irritation values of the mixture are reduced by a factor of three. Application of the silicone phosphate ester to the skin or eye either before or immediately after the application of the fatty alcohol sulfate or fatty alcohol ether sulfate does not appreciably reduce the irritation values encountered. This is strong evidence for the formation of a complex which provides the protection. Generally, complexes form when anionic and cationic compounds are mixed. This is because of the opposite charges on the molecules. Generally, these complexes lose their surfactant properties such as foam and wetting. These complexes also do not mitigate irritation. Surprisingly, we have learned that there is a complex formed between the anionic fatty alcohol sulfate or fatty alcohol ether sulfate and the anionic silicone phosphate ester which mitigates irritation.

(2) Object of the Invention

It is the object of the present invention to provide a complex which mitigates irritation of fatty alcohol sulfates or fatty alcohol ether sulfates to the eyes and skin by incorporating a series of novel phosphated silicone polymers. The ratio of phosphate to sulfate can range from 1:1 to 0.01 to 1.

It is another objective of the current invention to provide a process for treating the hair and skin with the complex between the fatty alcohol sulfate or ether sulfate and the phosphated silicone polymer. The process comprises (1) formation of the complex by mixing together silicone phosphate ester and fatty alcohol sulfate or fatty alcohol ether sulfate and silicone phosphate ester, (2) contacting the hair or skin with an effective cleansing amount of the complex and (3) removing excess complex by rinsing with water. The ratio of phosphate to sulfate can range from 1:1 to 0.01 to 1.

(3) Description of the Arts and Practices

Fatty alcohol sulfates and fatty alcohol ether sulfates are a class of anionic detergents which are used very commonly in shampoo, skin cleanser and other applications which require detergency properties. These materials while outstanding detergents are quite irritating to skin and eyes. This is due in part to the fact that these materials de-fat the skin and eyes. That is they remove the naturally occurring fatty materials found in the normal hair and skin and leave the skin or eyes in a clean albeit irritated state.

The inclusion of ethylene oxide into the sulfate has a marginal effect upon irritation, reducing it somewhat. This reduction is obtained at the expense of cleansing properties. It was not until the present invention that it was realized that formation of a fatty alcohol sulfate or fatty alcohol ether sulfate and silicone phosphate ester complex effectively reduced irritation and did not adversely affect the performance of the detergent properties of the sulfate.

U.S. Pat. No. 5,070,171 issued to O'Lenick, Jr. and U.S. Pat. No. 5,149,762 likewise issued to O'Lenick, Jr. disclose the technology used to prepare the silicone phosphate esters useful as one ingredient in preparing the complex of the present invention.

THE INVENTION

Summary of the Invention

The present invention relates the formation of a complex which mitigates the irritation of fatty alcohol sulfates or fatty alcohol ether sulfates without adversely affecting the surfactant properties of the fatty sulfates. The complex is prepared by mixing fatty alcohol sulfates or fatty alcohol ether sulfates with silicone phosphate esters. These complexes exhibit the same surfactant properties as the fatty alcohol sulfate or fatty alcohol ether sulfate, but surprisingly have the eye and skin irritation reduced by 3 to 5 times, when tested using standardized eye and skin irritation studies.

The complex of the invention is represented by the following formula;

$(f + 1) M^\oplus$

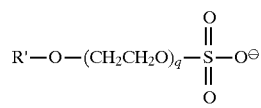

wherein
R is

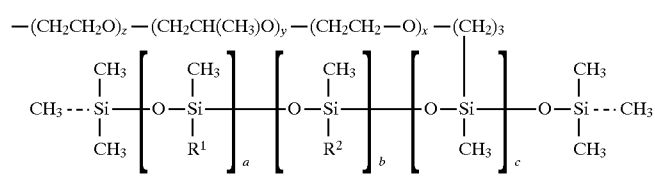

a is an integer from 0 to 200;

b is an integer from 0 to 200;

c is an integer from 1 to 200;

$R^1$ is $CH_3$;

n is an integer from 0 to 10;

$R^2$ is $-(CH_2)_3-(OCH_2CH_2)_x-(OCH_2CH(CH_3))_y-(OCH_2CH_2)_z-OH$;

x, y and z are integers and are independently selected from 0 to 20;

e and f range from 1 to 2 with the proviso that e+f=3;

M is selected from H, Na, K, Li or $NH_4$;

R' is alkyl having from 10 to 20 carbon atoms;

q is an integer ranging from 0 to 6.

The complexes of the present invention are prepared by mixing together the silicone phosphate ester and the fatty alcohol sulfate or fatty alcohol ether sulfate in aqueous solution ranging from 30 to 90 percent water. The ratio of phosphate to sulfate can range from 1:1 to 0.01 to 1.

The complex is applied to the skin or eye and the irritation is compared to that of the fatty alcohol sulfate or fatty alcohol ether sulfate alone.

As a control the phosphate ester was applied to the skin before addition of the fatty alcohol sulfate or fatty alcohol ether sulfate to see if there was any mitigation in irritation. There was no mitigation using this procedure.

As another control the fatty alcohol sulfate or fatty alcohol ether sulfate was applied to the skin immediately before addition of the silicone phosphate ester to see if there was any mitigation in irritation. There was no mitigation using this procedure.

These findings confirm the existence of a irritation mitigating complex which needs to be formed prior to application on the eye or skin.

SILICONE PHOSPHATE ESTERS

The silicone phosphate esters used in the preparation of the complexes of the present invention are prepared by reaction of a hydroxyl containing silicone polymer with a suitable phosphating reagent.

One method of placing the reactive hydroxyl containing silicone polymer is to react silanic hydrogen containing polymer with allyl alcohol or allyl alcohol alkoxylate monomer.

Procedures for this reaction are well known to those skilled in the art. U.S. Pat. No. 4,083,856 describe suitable processes.

EXAMPLES

Vinyl Intermediate Compounds

Compounds of this class are prepared by alkoxylation of allyl alcohol using methods well known to those skilled in the art. The following are some of the many compounds which can be used to make the products of this invention.

$CH_2-CH-CH_2-O-(CH_2-CH_2-O)_x-(CH_2-CH(CH_3)-O)_y-(CH_2-CH_2-O)_z-H$

| Designation | x | y | z | Molecular Weight |
|---|---|---|---|---|
| A | 3 | 0 | 0 | 189 |
| B | 9 | 27 | 3 | 2,178 |
| C | 11 | 3 | 0 | 718 |

-continued $CH_2-CH-CH_2-O-(CH_2-CH_2-O)_x-(CH_2-CH(CH_3)-O)_y-(CH_2-CH_2-O)_z-H$

| Designation | x | y | z | Molecular Weight |
|---|---|---|---|---|
| D | 0 | 0 | 0 | 57 |
| E | 20 | 20 | 20 | 2,940 |
| F | 20 | 0 | 0 | 880 |
| G | 10 | 10 | 10 | 1,470 |

Preparation of Intermediates

Silicone intermediates of the type used to make the compounds of this invention are well known to those skilled in the art. International Publication (Silicone Alkylene Oxide Copolymers As Foam Control Agents) WO 86/0541 by Paul Austin (Sep. 25, 1986) p. 16 (examples 1 to 6) teaches how to make the following intermediates, and is incorporated herein by reference.

Hydrosilation of Intermediates

Silanic Hydrogen Containing Compounds

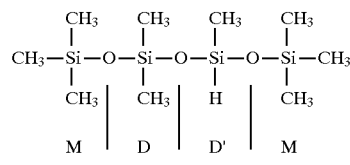

Group Designations

| Example | Austin Example | Group Designation | Average Molecular Weight | Equivalent Molecular Weight |
|---|---|---|---|---|
| 1 | 1 | MD 20 D' 3.2 M | 1,850 | 551 |
| 2 | 4 | MD 160 D' 5 M | 24,158 | 4,831 |
| 3 | 6 | MD 20 D' 10 M | 2,258 | 225 |

Hydrosilation Compounds

The hydrosilation reaction used to make the compounds of this invention are well known to those skilled in the art. Reference; International Publication (Silicone Alkylene Oxide Copolymers As foam Control Agents) WO 86/0541 by Paul Austin (Sep. 25, 1986) p. 19.

Example 4

To a liter three necked round bottom flask fitted with a mechanical agitator, thermometer with a Therm-o-watch temperature regulator, nitrogen sparge tube vented reflux condenser and heating mantle is added 189.0 grams of Vinyl Intermediate Example # A. Next add 225 grams of Silanic Hydrogen Containing Compound Example #3 and 3,000 grams of toluene. Heat to 115° C. to remove azeotropically remove any water 200 ml of toluene. The temperature is reduced to 85° C. and ml of 3% H 2 PtCl 6 in ethanol is added. Light is then excluded from the flask by covering it with a black cloth. An exotherm is noted to about 95° C., while the contents are stirred about 2 hours. During this time silanic hydrogen concentration drops to nil. Cool to 65° C. and slowly add 60 g of sodium bicarbonate allow to mix overnight and filter through a 4 micron pad. Distill off any toluene at 100° C. and 1 torr.

Example 5–10

The above procedure is repeated, only this time replacing both silanic hydrogen compound #3 with the specified number of ms of the specified silanic hydrogen compound and the vinyl intermediate example A with the specified number of grams of the specified vinyl intermediate.

| | Vinyl Intermediate | | Silanic Hydrogen Compound | |
|---|---|---|---|---|
| Example | Example | Grams | Example | Grams |
| 4 | A | 189.0 | 1 | 551.0 |
| 5 | B | 2,178.0 | 2 | 4,831.0 |
| 6 | C | 718.0 | 3 | 225.0 |
| 7 | D | 57.0 | 1 | 551.0 |
| 8 | E | 2,940.0 | 2 | 4,831.0 |
| 9 | F | 880.0 | 3 | 225.0 |
| 10 | G | 1,470.0 | 1 | 551.0 |

PHOSPHATION

Phosphating Agents

Polyphosphoric Acid (PPA) is 115% phosphoric acid. When used as a phosphating agent in gives more mono ester than the phosphorus pentoxide.

Phosphorus pentoxide is $P_2O_5$. It is more aggressive in phosphation and results in more diester.

The silicone phosphates useful as raw materials for the practice of this invention can be prepared by reacting the hydroxyl containing silicone polymer with a suitable phosphating agent. Preferred phosphating reagents are polyphosphoric acid and phosphorus pentoxide.

The preparation of the novel silicone phosphates of this invention from the hydroxy silicone compounds can be illustrated by the following reaction in which R is the hydroxy silicone compound.

Phosphation Reaction Sequence

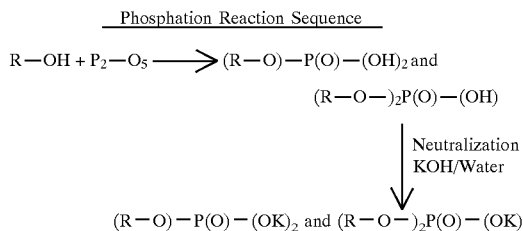

It will be understood by the above reaction that the product of phosphation, using polyphosphoric acid or phosphorus pentoxide give a mixture of mono and di ester.

The following examples further illustrate the objects and advantages of this invention, though it should be understood that the various reactants and amounts thereof, reaction conditions, and other details are merely illustrative and should not be construed to unduly limit this invention.

GENERAL PROCEDURE

The specified amount of hydroxy silicone compound (Examples 4–10) is added to a suitable reaction vessel. The specified amount of either polyphosphoric acid or phosphorus pentoxide is charged to under good agitation over a 2 hr. period. The exothermic reaction raises the temperature of the period. The exothermic reaction raises the temperature of the mixture to about 70° C. After 1 hour slowly raise the temperature to 100° C. and hold 2–4 hours.

| | Hydroxy Silicone | | Polyphosphoric Acid |
|---|---|---|---|
| Example | Example | Grams | Grams |
| 11 | 4 | 740.0 | 56.5 |
| 12 | 5 | 7009.0 | 56.5 |
| 13 | 6 | 943.0 | 56.5 |
| 14 | 7 | 608.0 | 56.5 |
| 15 | 8 | 7771.0 | 56.5 |
| 16 | 9 | 1105.0 | 56.5 |
| 17 | 10 | 2021.0 | 56.5 |

Phosphorus Pentoxide

| | Hydroxy Silicone | | Phosphorus Pentoxide |
|---|---|---|---|
| Example | Example | Grams | Grams |
| 18 | 11 | 798.0 | 36.0 |
| 19 | 12 | 7067.0 | 36.0 |
| 20 | 13 | 1001.0 | 36.0 |
| 21 | 14 | 666.0 | 36.0 |
| 22 | 15 | 7829.0 | 36.0 |
| 23 | 16 | 1163.0 | 36.0 |
| 24 | 17 | 2079.0 | 36.0 |

The compounds of examples 11–24 are neutralized to pH 7 with 20% aqueous base. The following bases are used; NaOH, KOH, LiOH, NH 4 OH.

| Example | Phosphated Silicone Example | Base Type |
|---|---|---|
| 25 | 11 | KOH |
| 26 | 12 | NaOH |
| 27 | 13 | LiOH |
| 28 | 14 | NH4OH |
| 29 | 15 | KOH |
| 30 | 16 | NaOH |
| 31 | 17 | KOH |
| 32 | 19 | NaOH |
| 33 | 19 | KOH |
| 34 | 20 | NaOH |
| 35 | 21 | KOH |
| 36 | 22 | NaOH |
| 37 | 23 | KOH |
| 38 | 24 | NaOH |

Fatty Alcohol Sulfates and Fatty Alcohol Ether Sulfates

These materials are items of commerce available from a variety of sources including Henkel Corporation and Stepan.

| Example | R' | q | N | Description |
|---|---|---|---|---|
| 39 | C10 H21 | 0 | K | Potassium Decyl Sulfate |
| 40 | C12 H25 | 0 | Na | Sodium Lauryl Sulfate |
| 41 | C14 H29 | 0 | Li | Lithium Myristyl Sulfate |
| 42 | C16 H33 | 0 | NH4 | Ammonium Cetyl Sulfate |
| 43 | C18 H37 | 0 | Na | Sodium Stearyl Sulfate |
| 44 | C10 H21 | 3 | K | Potassium Deceth (3) Sulfate |

-continued

| Example | R' | q | N | Description |
|---|---|---|---|---|
| 45 | C12 H25 | 3 | Li | Lithium Laureth (3) Sulfate |
| 46 | C14 H29 | 3 | NH4 | Ammonium Myreth (3) Sulfate |
| 47 | C16 H33 | 6 | Na | Sodium Ceteth (6) Sulfate |
| 48 | C18 H37 | 6 | Na | Sodium Steareth (6) Sulfate |
| 49 | C20 H41 | 6 | K | Potassium Beheneth (6) Sulfate |
| 50 | C12 H25 | 4 | Na | Sodium Laureth (4) Sulfate |

The number in parenthesis is the value of "q". Therefore Sodium Laureth (4) Sulfate is

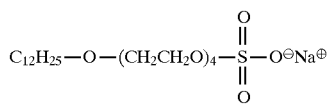

COMPLEX FORMATION

The complex between the fatty alcohol sulfate or fatty alcohol ether sulfate and silicone phosophate ester is obtained by mixing the two components in aqueous solution. The preferred concentration of water is between 50 and 80% by weight.

Example 51

100.0 grams of fatty alcohol sulfate (example 39) is added to 200.0 grams of water. Next, 1.0 grams of silicone phosphate (example 25) is added under good agitation. The resulting complex is found to have very low eye and skin irritation compared to the fatty alcohol sulfate alone.

Examples 52–64

Example 51 is repeated, only this time substituting the specified type and amount of fatty alcohol sulfate or fatty alcohol ether sulfate for example 39 and substituting the specified type and amount of silicone phosaphate ester for example 25.

| | Fatty Sulfate | | Silicone Phosphate | |
|---|---|---|---|---|
| Example | Example | Amount | Example | Amount |
| 52 | 40 | 100.0 | 26 | 100.0 |
| 53 | 41 | 100.0 | 27 | 50.0 |
| 54 | 42 | 100.0 | 28 | 25.0 |
| 55 | 43 | 100.0 | 29 | 1.0 |
| 56 | 44 | 100.0 | 30 | 100.0 |
| 57 | 45 | 100.0 | 31 | 75.0 |
| 58 | 46 | 100.0 | 32 | 100.0 |
| 59 | 47 | 100.0 | 33 | 50.0 |
| 60 | 48 | 100.0 | 34 | 5.0 |
| 61 | 49 | 100.0 | 35 | 100.0 |
| 62 | 50 | 100.0 | 36 | 75.0 |
| 63 | 39 | 100.0 | 37 | 50.0 |
| 64 | 40 | 100.0 | 38 | 10.0 |

Test Protocol

Primary Skin Irritation was run using the protocol outlined in FHSLA 16 C.F.R. 1500.41

Applications Results

| Test Example | Rating | Rating |
|---|---|---|
| 40 | 2.7 | Moderate Primary Irritant |

Sodium Lauryl Sulfate is itself a moderate skin irritation.

| Test Example | Rating | Rating |
|---|---|---|
| 52 | 0.3 | Non-primary Irritant |

Sodium Lauryl Sulfate is itself a moderate skin irritation, has it's irritation reduced to non-irritating status by addition of silicone phosphate.

| Test Example | Rating | Rating |
|---|---|---|
| 64 | 0.4 | Non-primary Irritant |

Sodium Lauryl Sulfate is itself a moderate skin irritation, has it's irritation reduced to non-irritating status by addition of silicone phosphate.

The skin was pretreated with silicone phosphate example 38 followed by treatment with fatty sulfate example 40. The resulting skin irritation data was 2.3. The pretreatment with silicone phosphate is not an effective irritation mitigant.

The skin was pretreated with fatty sulfate example 40 followed by treatment with silicone phosphate example 38. The resulting skin irritation data was 2.6. The post treatment with silicone phosphate is not an effective irritation mitigant.

Unexpectedly, only when the two are combined in a complex is the desired mitigation of skin irritation observed.

The same reduction in irritation values are observed in eye irritation studies. Again, in order to be effective the complex must be applied. The effect is not observed when the two are applied separately, regardless of the order of application.

What is claimed:
1. A process for the mitigating of irritation which comprises application to the skin of an effective irritation mitigating amount of a complex of the following formula;

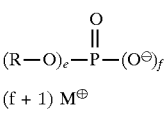

(f + 1) M$^{\oplus}$

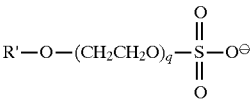

wherein

R is

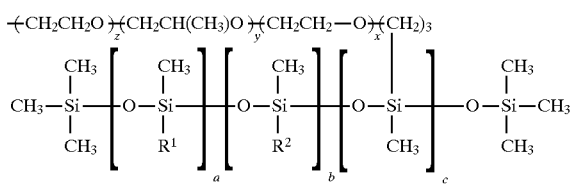

a is an integer from 0 to 200;
b is an integer from 0 to 200;
c is an integer from 1 to 200;
$R^1$ is $CH_3$;
n is a n integer from 0 to 10;.
$R^2$ is —$(CH_2)_3$—$(OCH_2CH_2)_x$—$(OCH_2CH(CH_3))_y$—$(OCH_2CH_2)_z$—OH
x, y and z are integers and are independently selected from 0 to 20;
e and f range from 1 to 2 with the proviso that e+f=3;

M is selected from H, Na, K, Li or NH4;
R' is alkyl having from 10 to 20 carbon atoms;
q is a n integer ranging from 0 to 6.

2. A process of claim 1 wherein the effective irritation mitigating amount ranges from 0.01 to 20.0%, the % by weight is based upon total composition.

3. A process of claim 1 wherein q is 0 to 3.

4. A process of claim 1 wherein R' is alkyl having from 12 to 18 carbon atoms.

5. A process of claim 1 wherein R' is alkyl having 12 carbon atoms.

6. A process of claim 1 wherein R' is alkyl having 14 carbon atoms.

7. A process of claim 1 wherein R' is alkyl having 16 carbon atoms.

8. A process of claim 1 wherein R' is alkyl having 18 carbon atoms.

9. A process of claim 1 wherein M is Na.

* * * * *